United States Patent [19]

Shikinami et al.

[11] Patent Number: 5,039,774
[45] Date of Patent: Aug. 13, 1991

[54] LIQUID SEGMENT POLYURETHANE GEL AND COUPLERS FOR ULTRASONIC DIAGNOSTIC PROBE COMPRISING THE SAME

[75] Inventors: Yasuo Shikinami; Kaoru Tsuta; Masahiko Taniguchi; Hidekazu Boutani, all of Osaka, Japan

[73] Assignee: Takiron Co., Ltd., Osaka, Japan

[21] Appl. No.: 530,517

[22] Filed: May 30, 1990

Related U.S. Application Data

[62] Division of Ser. No. 355,702, May 23, 1989, Pat. No. 4,966,953.

[30] Foreign Application Priority Data

Jun. 2, 1988 [JP] Japan .................................. 63-135976
Nov. 11, 1988 [JP] Japan .................................. 63-286520

[51] Int. Cl.$^5$ ................................................ C08G 18/10
[52] U.S. Cl. ...................................... 528/60; 128/632; 128/653 R; 128/660.01; 128/660.02; 128/660.06; 128/662.03

[58] Field of Search .................... 528/60, 66; 128/632, 128/653 R, 660.01, 660.02, 660.06, 662.03

[56] References Cited

FOREIGN PATENT DOCUMENTS 1190446 5/1970 United Kingdom .
2036504 6/1980 United Kingdom .

Primary Examiner—Maurice J. Welsh
Attorney, Agent, or Firm—Sughrue, Mion, Zinn, Macpeak & Seas

[57] ABSTRACT

A one-component system polyurethane gel and a coupler for ultrasonic diagnostic probes comprising the same are disclosed. The gel is obtained by reacting a polyol having a room temperature liquid alkylene oxide chain and/or a polyurethane polyol prepolymer having a room temperature liquid alkylene oxide chain with a polyurethane polyisocyanate prepolymer having a room temperature liquid alkylene oxide chain. The gel causes no bleeding or evaporation of a dispersion medium and is therefore excellent in safety to the human body and preservation stability.

6 Claims, 4 Drawing Sheets

LIQUID SEGMENT POLYURETHANE GEL AND COUPLERS FOR ULTRASONIC DIAGNOSTIC PROBE COMPRISING THE SAME

This is a divisional of application Ser. No. 07/355,702 filed May 23, 1989 and now U.S. Pat. No. 4,966,953.

FIELD OF THE INVENTION

This invention relates to a liquid segment polyurethane gel suitable for medical or sanitary use and to a coupler for a ultrasonic diagnostic probe comprising the same.

BACKGROUND OF THE INVENTION

In general, a gel, in a broad sense of the word, is a solidified substance in which colloid particles or polymer solutes lose an independent molecular mobility due to their interactions to form molecular aggregates. When such a substance contains a dispersion medium, the medium serves to inhibit the colloid particles or polymer substances from separating as agglomerated masses so as to maintain the system in a non-fluid semisolid state. Such a system in which a gel-forming substance (dispersed substance) includes a dispersion medium is called lyogel, that is a "gel" in its narrow sense.

In other words, the terminology "gel" in its narrow sense means a two-component disperse system composed of a solid dispersed substance and a liquid dispersing medium, the system as a whole being a non-fluid semisolid and semiliquid substance. Systems containing water as a dispersing medium are called hydrogels, and systems containing organic solvents are called organogels.

The dispersed substance, i.e., a solid supporting the fundamental structure of a gel, is in many cases an aggregate of a polymer having a crosslinked structure on a molecular level or a fine particle level. It is a well known fact that forces of not only first-order bonding (e.g., covalent bonding and inoic bonding) but second-order bonding (e.g., hydrogen bonding and dipole interaction) take part in supporting the three-dimensional gel structure. Base on this fact, an extrmely large number of examples are implicit in the gel of crosslinked polymers containing a dispersion medium. Among the gels of this type, many kinds of hydrogels containing water as a dispersion medium are known, and extensive studies on hydrogels of synthetic polymers have recently been conducted pursuing the possibility of application to medical, sanitary and agricultural fields.

Polymer compounds which can form hydrogel include, for example, natural polymers, e.g., starch, gum arabic, karaya gum, tragacanth gum, pectin, pullulan, arum root, dextran, sodium alginate, amylose, carrageenan, chitin, gelatin, and casein; semisynthetic polymers, e.g., methyl cellulose, ethyl cellulose, hydroxymethyl cellulose, hydroxy ethyl cellulose, hydroxypropyl cellulose, carboxymethyl cellulose, propylene glycol alginate; and synthetic polymers, e.g, polyvinyl alcohol and its modification products, polyvinyl pyrrolidone, (sodium) polyacrylate, (sodium) polymethacrylate, polyacrylamide, poly-2-hydroxyethyl methacrylate, poly-N-dimethylaminoethyl methacrylate, polyglutamic acid, polyaminostyrene, polyethylene oxide-polypropylene oxide copolymers, styrene-maleic anhydride (or its Na or $NH_4$ salt) copolymers, vinyl acetate-crotonic acid copolymers, vinyl acetate-maleic anhydride copolymers, isobutenemaleic anhydride copolymers, polymethacrylic acidpolyvinyl chloride copolymers, hydrolyzates of polyacrylonitrile, high polyelectrolytes, such as polyvinylbenzyltrimethylammonium and polystyrene sulfonic acid (or a Na salt), and their complexes, and hydrophilic polyurethane.

While polymers which can form an organogel have not received as extensive an investigation as the hydrogels, organogels comprising the above-recited polymers capable of forming a hydrogel and a solvent, e.g., alcohols, acetone, and an alcohol-water mixed solvent, have been studied for their various physical properties. Physical properties of a system comprising a vulcanized synthetic rubber and an oil have hitherto been studied as a representative example of organogels. For example, polypropylene fibers as oil absorbents belong to this category. In recent years, from the viewpoint of interpenetrate polymer network (IPN), polymers having a three-dimensional network structure have been a subject of studies as systems of swelling with various organic dispersion media.

Any of these known gel systems consist of two components of a solid dispersed substance and a liquid dispersion medium, the system retention greatly depending on the interaction between these two components. That is, the liquid functions to prevent the polymer network from degradation followed by formation of compact masses, while the polymer network functions to retain the liquid. Therefore, there is no restraint by first-order bonding due to covalent bonding, though these two components are in some secondary interaction with each other.

The two-component system gel is coagulated with the dispersion medium being separated to become a xerogel (coagel), which re-absorbs a solvent and is thus swollen to form a gel. In other words, the dispersion medium of the two-component system gel can make its entrance in and exit from the system. For example, a hydrogel, which contains a large quantity of water, gradually releases its water content on standing in air and finally becomes a xerogel particularly in exceedingly dry air.

It is however very difficult to absolutely dry a hydrogel, and water more or less remains therein due to moisture absorption. This is attributed to strong bonding between the hydrogel-forming high polymer and water. In this connection, water in which any chemical bonding participates is called bound water, otherwise water being called free water. It is the former that makes it difficult to absolutely dry a hydrogel and causes moisture absorption. The same phenomenon can be seen in organogels containing volatile solvents, e.g., acetone, methyl alcohol, ethyl alcohol, and ethyl acetate. It is therefore difficult to maintain the dispersed substance and the dispersion medium of this type of gel in a constant state for a long period of time in an open system.

In the case of oil gels comprising a vulcanized rubber and a large quantity of an oil, evaporation of the dispersion medium does not occur as long as the oil has a high boiling point or a low vapor pressure. Nevertheless, since the bonding between rubber and oil is essentially weak and a large proportion of the oil does not take part in this bonding, the oil easily bleeds out of the system. Therefore, it is difficult to handle these types of gels containing a large quantity of a solvent while maintaining a constant ratio of the dispersed substance and the solvent. In addition, because the solvent sticks to hands on handling, these gels are not suitable as medical or sanitary materials that may be brought into contact or attachment with the human body even for a short time from the standpoint of preservation stability and hygiene.

Quite recent years have seen studies on use of a gel as a contact medium (coupler) for a probe for ultrasonic diagnosis. As is well known, ultrasonic diagnosis is widespread because the apparatus therefor is cheaper than those for any other diagnostic methods and it can be carried out simply without imposing a burden on a patient. The ultrasonic diagnostic apparatuses are classified by scanning mode as a linear type, a convex type, a sector type, and a trapezoid type, which are selected according to the site and purpose of diagnosis. A probe is chosen in agreement with the scanning mode of the apparatus. Of these scanning modes, a mechanical sector scanning system in which ultrasonic waves from a large aperture (a site for sending and receiving ultrasonic waves) are sharply focused on the part to be inspected has made it possible to detect delicate changes of the tissue. While the part which can be inspected by this system varies depending on the frequency employed, the system is greatly effective in making diagnosis particularly of the surficial tissues, such as the mammary gland, the thyroid gland, and the carotid artery.

The probe to be used in the mechanical sector scanning system has a cylindrical form, and the part to be inspected has conventionally been scanned with the probe having fitted at the end thereof a container made of a synthetic resin in which degassed water is sealed so as to follow the shape of the skin (a so-called water bag). However, preparation of degassed water and sealing of the degassed water into the container are very complicated. Further, some air which unavoidably enters into the interface between the tip of the probe and degassed water frequently causes noise or artifacts, resulting in failure to obtain a clear image. Further, it is necessary to apply jelly to the skin in order to prevent formation of an interfacial air layer between the skin and the container.

Under the situation stated above, studies have been made to use a gel as a contact medium which adds a function of acoustic adjustment for obtaining a clearer diagnositic image. Hydrogels so far proposed for this particular use include a gel of a glycerin aqueous solution containing a cellulose ether compound as disclosed in JP-A-61-146234 (the term "JP-A" as used herein means an "unexamined published Japanese patent application"); a gel of a high molecular weight polymer, e.g., polyacrylamide, polyvinyl alcohol, and sodium polyacrylate, which exhibits sufficient strength and water retention and has a water content of 70% or more as disclosed in JP-A-59-82838, and a gel comprising polypropylene glycol and polyvinyl pyrrolidone as disclosed in JP-A-59-49750. Recent studies have been directed to a hydrogel comprising a polyvinyl alcohol/-polyvinyl pyrrolidone/water system to which a small amount of sulfuric acid is added as reported in Polymer Preprints Japan, Vol. 36, No.3 (1987).

Organogels comprising a vulcanized styrenebutadiene copolymer or a silicone resin to which liquid paraffin is added have partly been put into practical use.

However, use of these gels as a contact medium for ultrasonic diagnostic probes gives rise to various problems. The hydrogels have poor preservation stability, failing to maintain a constant composition because free water, a dispersion medium, is evaporated in air. Besides, hydrogels generally lack extensibility, are liable to suffer damages due to stretching, scratching, and abrasion, and are brittle and easy to break and therefore do not withstand repeated use. When a jelly having a high water content is applied to the skin for the purpose of preventing entrance of air between the gel and the skin to ensure intimate contact, and the gel is used thereon, water resistance of the gel is unreliable. Existence of a large quantity of free water leads to noise generation and frequency dependence. Further, contact media comprising a hydrogel are prepared by swelling a powderous polymer substance with water to form granular masses and joining the interfaces of the polymer masses so as to mold the masses into a larger shape, such as blocks, sheets, profiles, etc. The thus molded articles essentially contain particle-particle boundaries. When light or sound passes through the molded article, such boundaries cause absorption, irregular reflection or multiple reflection of light or sound.

On the other hand, organogels containing an oil are more practical because they have high boiling points and are therefore free from troubles due to evaporation of the dispersion medium. However, since they contain an excess dispersion medium which is weak in bonding to a gel-forming rubber, the excess oil easily and unlimitedly bleeds out. When the organogel is brought into intimate contact with the skin or direct contact with the heart for ultrasonic body section examination during cardiac operations, the oil bled out from the gel remains on the skin or in the body, giving serious problems of safety and an unpleasant feel.

The present invention provides a new type gel which is a one-component system gel. This gel is deviated from a conventional concept in molecular structure (two-component system). Any publication with respect to such a new type gel cannot be found.

SUMMARY OF THE INVENTION

One object of this invention is to provide a one-component system polyurethane gel which is excellent in safety to the human body and preservation stability without being accompanied by bleeding or evaporation of the dispersion medium.

Another object of this invention is to provide a one-component system polyurethane gel which has a low modulus and satisfactory resistance to tension, scratches and abrasions and therefore withstands repeated use as a contact medium.

Still another object of this invention is to provide a one-component system polyurethane gel which contains extremely reduced internal strain and does not cause absorption, irregular reflection or multiple reflection of light or sound due to particle-particle boundaries as observed in two-component system hydrogels.

Yet another object of this invention is to provide a coupler for an ultrasonic diagnostic probe, which exhibits excellent adhesion to both the probe and the skin and provides a clear image free from noise and artifacts.

A further object of this invention is to provide a coupler for an ultrasonic diagnostic probe, which has a rate of ultrasonic wave transmission and an acoustic impedance approximate to those of the human body tissues and is less dependent on frequency.

A still further object of this invention is to provide a coupler for an ultrasonic diagnostic probe, which is highly safe to the human body and does not cause allergic reactions and the like even when brought into contact with the human body for an extended period of time.

Yet a further object of this invention is to provide a practical and economical coupler for an ultrasonic diagnostic probe, which is easy to fit to or to remove from the probe and can be used repeatedly.

The above objects of this invention can be accomplished by using a novel one-component system elastic gel comprising segmented polyurethane all of which have an alkylene oxide chain which is liquid at room temperature.

The present invention relates to a polyurethane gel having segments which are liquid at room temperature, which is obtained by reacting a polyol having an alkylene oxide chain that is liquid at room temperature (hereinafter referred to as room temperature liquid (AO) chain) and/or a polyurethane polyol prepolymer having a room temperature liquid (AO) chain with a polyurethane polyisocyanate prepolymer having a room temperature liquid (AO) chain.

The present invention further relates to a coupler for a probe for ultrasonic diagnosis which comprises the above-described liquid segment polyurethane gel (hereinafter referred to as polyurethane gel).

That is, the one-component system gel of the present invention comprises segmented polyurethane of an interpenetrated network type in which a room temperature liquid (AO) chain serves as a dispersion medium for gel formation and an isocyanate compound serves as a skeleton for gel formation, the both being bonded through first-order chemical bonding. The coupler of the present invention comprising the above-described one-component system elastic gel has a socket into which a probe for ultrasonic diagnosis is inserted with intimate contact and a smooth part for planar contact with the skin.

The other objects, characteristics, and advantages of the present invention will be apparent from the description hereinafter given.

DETAILED DESCRIPTION OF THE INVENTION

The one-component system elastic gel comprising liquid segmented polyurethane according to the present invention can be obtained by reacting at least one polyol represented by any of formulae (II) to (IV) shown below and/or at least one polyurethane polyol prepolymer represented by formula (I) shown below with at least one polyurethane polyisocyanate prepolymer represented by any of formulae (V) to (VIII) shown below.

(I)

wherein $R_1$ and $R_2$ each represents an alkyl group, an alicyclic group, or an aromatic group; and (AO) represents an alkylene oxide chain.

(II)

wherein (AO) is as defined above; and l represents an integer of 1 or 4.

(III)

wherein (AO) is as defined above.

$$R'O—(AO)—H \qquad (IV)$$

wherein (AO) is as defined above; and R' represents a hydrogen atom, an alkyl group, an alicyclic group, or an aromatic group.

(V-1)

wherein (AO) is as defined above; and R represents an alkyl group, an alicyclic group, or an aromatic group.

(V-2)

wherein (AO) and R are as defined above.

(VI)

wherein (AO), R, and l are as defined above.

(VII)

wherein (AO) and R are as defined above.

(VIII)

wherein (AO) and R are as defined above.

$R_1$, $R_2$, and R represent a skelton for isocyanate. Examples of $R_1$, $R_2$, and R include, for example, Φ-phenylene, toluylene, diphenylmethane, naphthalene, hexamethylene, tetramethylene, lysine, xylylene, hydrogenated toluylene, hydrogenated diphenylmethane, dicyclohexyldimethylmethane, diethylfurmarate, and isophorone.

R' represents a hydrogen atom, an alkyl group, an alicyclic group, or an aromatic group. When formula (IV) is a monofunctional group, it reacts with —NCO group to form a branched molecule terminated at one end. This branched (AO) is liquid and it tends to form an elastic gel as it is easy to conduct a free rotation movement of the molecule. For this reason, it is better that the size of the terminal reacted formula (IV) molecule is not so large. For example, an alkyl group having a low molecular weight (e.g., methyl, ethyl, propyl, and butyl), an alkyl group having a low melting point (e.g., oleyl, palmityl, and a branched form thereof), a monocyclic aromatic group (e.g., benzene, toluene, and xylene), and a monocyclic alicyclic group (e.g., cyclohexane and cyclohexanone) are used.

Each of these prepolymers contains —OH or —NCO as a functional group, and reaction of these functional groups forms a segmented polyurethane having an interpenetrated network.

The polyurethane polyol prepolymer represented by formula (I) is a reaction product of a polyether polyol and a diisocyanate. Both of the terminal components comprise a hydroxyl-terminated polyether polyol. The diisocyanate compounds to be used are the same as those used in the polyurethane polyisocyanate prepolymers hereinafter described. Examples of the diisocyanate compounds include Φ-phenylene diisocyanate, 2,4-toluylene diisocyanate (TDI), 4,4'-diphenylmethane diisocyanate (MDI), naphthalene 1,5-diisocyanate, hexamethylene diisocyanate (HMDI), tetramethylene diisocyanate (TMDI), lysine diisocyanate, xylylene diisocyanate (XDI), hydrogenated TDI, hydrogentated MDI, dicyclohexyldimethylmethane p,p'-diisocyanate, diethylfumarate diisocyanate, and isophorone diisocyanate (IPDI).

The polyol represented by formula (II) is an adduct obtained by adding a polyether polyol to glycerol (l=1) or sorbitol (l=4). The polyol represented by formula (III) is an adduct obtained by adding a polyether to trimethylopropane. Similarly, an adduct obtained by adding a polyether polyol to a polyhydric alcohol, e g., 1, 2, 6-hexanetriol trimethylolethane pentaerythritol (C(CH$_2$OH)$_4$), polyglycerin wherein n is a positive integer of from 2 to 30), or a partial ester thereof, can also be used.

The alkylene oxide chain as represented by (AO) may be a homopolymer or a block or random copolymer.

The alkylene oxide-containing polyether polyol represented by formula (IV) includes those terminated by a hydroxyl group at both ends thereof and those terminated by an alkyl group, an alicyclic group, or an aromatic group at one end and a hydroxyl group at the other end. These polyether polyols are easily available as commercial products.

The polyisocyanate prepolymer represented by formula (V-1) is a tetrafunctional tetraisocyanate obtained by connecting two molecules of a triisocyanate obtained by reacting trimethylolpropane with a diisocyanate via one molecule of (AO). Replacement of trimethylolpropane with glycerol yields the polyisocyanate prepolymer of formula (V-2). Since tetraisocyanates of this kind cannot be obtained by the reaction between two or three molecules of (AO) and two molecules of the triisocyanate, it is necessary to finely control the reaction by using (AO) in an amount of a little less than the chemical equivalent. As a result, the product contains unreacted triisocyanate, and the unreacted triisocyanate present in the prepolymer causes scatter in the of size of the segmented polyurethane molecules upon reacting the polyol, which sometimes favors with to control softness of the resulting elastic gel.

The polyisocyanate prepolymer represented by formula (VI) is a trifunctional or hexafunctional compound obtained by reacting the polyol of formula (II) with a diisocyanate. The prepolymer represented by formula (VIII) is a bifunctional compound obtained by reacting a polyether polyol and a diisocyanate.

The alkylene oxide chain. (AO) in the above structural formulae should be liquid at room temperature in order that the segmented polyurethane according to the present invention may have a semisolid and semiliquid low-modulus structure which forms an elastic gel at room temperature. Namely, it is best that all of the segments are liquid at room temperature, but the cases where not all but substantially all the segments are liquid are sometimes satisfactory. Should substantially all of the segments be solid, the molecular movement of the segments is blocked, and the alkylene oxide chain does not function as a dispersion medium in gelation of the system. If solid alkylene oxide chains, even in a small proportion, restrain free movement of other liquid segment molecules, the system does not undergo gelation. As long as the solid segments in a small proportion do not restrain free movement of other liquid segment molecules, the whole system seemingly exhibits a gelled state in some cases. In order to always obtain a gel structure, the construction in which all the segments are liquid is the most preferred. Further, for particular use as a coupler for an ultrasonic probe, it is preferable that all the segments are composed of a liquid.

The compounds constituting the alkylene oxide chain include polymethylene glycol, polyethylene glycol, polypropylene glycol, polybutylene glycol, polytetramethylene glycol, polypentamethylene glycol, polyhexamethylene glycol, and polyheptamethylene glycol. Among them, those which are liquid at room temperature and easily available are polyethylene glycol, polypropylene glycol, polybutylene glycol, and low-molecular weight polytetramethylene glycol.

In addition, copolymers of these compounds, such as and $(HO\!+\!CH_2CH_2O\!+\!_{l'}\!+\!CH_2CH_2CH_2CH_2O\!+\!_{m'}\!-\!(CH_2CH_2O\!+\!_{n'}\!\cdot\!H$, wherein l', m, and n' are an integer of 1 or more can also be used. Perferably, l' is an integer of 1 to 15, m is an integer of 1 to 40, and n' is an integer of 1 to 15. These copolymers may be either a block copolymer or a random copolymer. The segments per prepolymer may be composed of different kinds of alkylene oxide chains.

Because the alkylene oxide chains should be liquid at room temperature, the upper limit of their molecular weights is thus specified. On the other hand, if the alkylene oxide chain has too low of a molecular weight, though liquid, the distance between crosslinking points becomes too short thereby suppressing molecular movement of the segments and, as a whole, necessarily resulting in a high crosslinking density. Such being the case, the resulting gelled product is not liable to become a semiliquid and semisolid elastic gel but a solid elastomer. For this reason, the lower limit of the molecular weight of the alkylene oxide chain is also specified. To this effect, the polyethylene glycol to be used has a molecular weight of from 150 to 800, preferably from 200 to 600. Polypropylene glycol has a broad range of allowable molecular weights because it is still liquid with its molecular weight amounting to several tens of thousands. However, too long of a chain results in a small proportion of the terminal functional groups so that the reaction probability becomes low, thus requiring a considerably larger quantity of polyol over the theoretical quantity. A product obtained by using such a compound, however, exhibits high fluidity, poor shape retention, and excessive adhesiveness and hence cannot be considered as an elastic gel. For these reasons, a preferred molecular weight of polypropylene glycol ranges from 200 to 3000. Polybutylene glycol though similar to polypropylene glycol, has a relatively low viscosity, and its applicable molecular weight ranges from 300 to 5000, preferably from 400 to 3000. Polytetramethylene glycol becomes a solid with its degree of polymerization being high so that it is used with its molecular weight ranging from about 200 to 1000, preferably from 400 to 800. The copolymers of these compounds are used with their molecular weights ranging from several hundreds to several thousands.

The reaction between the polyol and the polyisocyanate will be described in detail.

Experience shows that the molecular aggregates having a gelled structure according to the present invention should satisfy requirements that they comprise relatively bulky molecules having an appropriate molecular weight and having a segment length that enables free movement or they have many freely movable molecules at the terminals of the linear chain thereof. Therefore, either one of the polyol and the polyisocyanate, each being used alone, should be bifunctional, and the other to be combined should be at least trifunctional. If either one of them is monofunctional, no chain linkage takes place. Reaction between bifunctional compounds is not suitable, because it produces a linear molecule. Namely, it is desirable to combine a bifunctional compound and at least a trifunctional compound, or to combine at least trifunctional compounds. It should be noted, however, that a combination of compounds having too high a functionality yields a product having an increased network chain concentration, thus requiring long liquid segments for gelation. From the viewpoint of the requirement that the segment should be liquid at room temperature and the probability of reaction, there is a limit on the segment length. Accordingly, a combination of these reactants which easily gives a desired gel is selected from bifunctional to tetrafunctional compounds. In particular, a combination of a bifunctional compound and a trifunctional compound is easy to prepare.

For fine control of physical properties of the gel, such as softness and elasticity, a monofunctional compound can be admixed as an internal dispersion medium. In cases where most of the alkylene oxide chains of the polyol and polyisocyanate prepolymer are composed of considerably long chains, a polyfunctional polyhydric alcohol or a polyfunctional isocyanate each containing no alkylene oxide segment may be used in combination to control the network chain structure.

The reaction ratio of the polyol and the polyisocyanate can be specified by the ratio of the respective terminal functional groups, i.e., an OH/NCO ratio. Since any —NCO group remaining unreacted would induce post-reactions, the OH/NCO ratio must be at least 1.

Considering that the gel system of the present invention is a one-component system in which a dispersed substance and a dispersion medium form covalent bonds within individual polymer molecules, the OH/NCO ratio is basically 1 or approximately 1. However, taking the actual reaction probability into account, since the reaction is between prepolymers, the OH/NCO ratio may be slightly more than 1 as long as the gel structure of the resulting product is within the scope of the present invention.

It should be understood that use of the polyol component in such a large quantity that would serve as a dispersion medium to swell the network structure, or a two-component system gel which cannot be formed without the aid of a plasticizer, etc. deviates from the spirit of this invention. It has been confirmed by experience that gels included in the scope of the present invention can be obtained with the OH/NCO ratio falling within a range of from 1.0 to 2.0, preferably from 1.0 to 1.5. In some cases, gels exhibiting seemingly the same physical behavior as those of this invention may be obtained even with the OH/NCO ratio being in the range of from 2 to 3, which is ascribed to the reaction probability dependent on molecular shape and morphological behavior of molecular aggregates. However, such gels not only involve the possibility of bleeding with the passage of time but also are inferior to those obtained at the OH/NCO ratio close to 1 in total physical properties. Hence, they also deviate from the spirit of the present invention. It should be noted, however, that in some cases the preferred gel can be obtained by mixing a gel having the OH/NCO ratio of 2 to 3 and a gel having the OH/NCO ratio of close to 1 in the total OH/NCO ratio of 1.0 to 2.0.

The molecular weights of the polyol and the polyisocyanate constituting the one-component system gel of the present invention vary widely depending on the kind of the alkylene oxide (AO), the kind and molecular shape of the isocyanate, and whether the (AO) is a homopolymer or a copolymer. In general, the molecular weight ranges from about 1,400 to 10,000, preferably from about 1,000 to 6,000, as to the polyurethane polyol prepolymer; from about 150 to 6,000, preferably from about 200 to 3,000, as to the polyol; and from about 500 to 10,000, preferably from about 800 to 5,000, as to the polyurethane polyisocyanate prepolymer.

If desired, the reaction rate can be controlled by using a catalyst for the reaction, such as dibutyltin dilaurate, a tertiary amine (e.g., trialkylamines, triethylenediamine), etc. in a adequate amount (usually from 0.01 to 1.0% by weight based on the total polymer weight).

The thus obtained elastic gel is a one-component system comprising segmented polyurethane of an interpenetrate network type which is gelled by room temperature liquid (AO) segments. In this one-component system gel, knots are formed by urethane bonds upon reaction between a room temperature liquid polyalkylene oxide (polyether polyol) having a suitable length for forming a semiliquid and semisolid gel and an isocyanate and the knots have branched banding points at appropriate positions to form a network structure. In other words, the liquid polyol is gelled by urethane bonds, and the gel-constituting liquid segments act as a dispersion medium. The proportion of (AO) which constitutes the elastic gel molecules per molecule ranges from about 75 to 90%, and it may be interpreted that the liquid segments swell the system 3.0 to 9.0 times. The elastic gel, as a matter of course, can be further swollen with various solvents having affinity for (AO) or the isocyanate-constituting molecules. In this case, the elastic gel in which the liquid segment molecules are folded and interlocked is solvated with a solvent having a strong affinity for the elastic gel whereby the liquid segments are extended and disentangled to bring about a swollen state under tension.

In the one-component system polyurethane gel according to the present invention, the polyol component serving as a dispersion medium is bound to the isocyanate component through first-order bonding by a covalent bond unlike the conventional two-component system gels in which a dispersion medium, i.e., water in hydrogels, solvents in solvent gels, or oils in oil gels, is bound to a dispersed substance through weak interactions. The gel of the invention is therefore free from evaporation or bleeding of a dispersion medium. It can hence retain its gelled state permanently even in open air, never returning to a xerogel. Owing to the freedom from bleeding, the dispersion medium of the gel does not stick to the human body or any other articles in contact with the gel so that the gel of this invention is of high safety and sanitation and is suited for used as medical or sanitary materials.

Further, because the gel comprises one component which is internally swollen with liquid segments, it undergoes neither changes of physical properties that often take place in two-component system gels due to migration of a dispersion medium accompanying temperature changes nor changes of composition due to evaporation of the dispersion medium and the like, thereby exhibiting excellent preservation stability.

Because the dispersion medium segments in the gel are bound to the gel-forming skeleton through first-order bonding and form folded and interlocked molecules, the gel is a low-modulus substance exhibiting sufficient extensibility and still yet possesses satisfactory mechanical properties, such as shape retention and resistance to abrasion, scratching and stretching. The gel can therefore be used repeatedly in practical application with economy.

Further, the first-order bonding of the dispersion medium segments brings about good heat resistance and prevents the gel from solidification at the freezing point as is observed in hydrogels, bringing about satisfactory freeze resistance.

Furthermore, since neither of the polyol component or the isocyanate component is a room temperature liquid prepolymer, a gelled product of desired size and shape (e.g., sheet, block, or profile) can be obtained by simply casting a mixture of these reactants in a desired mold. In the thus obtained elastic gel, internal strain is extremely reduced and there are no boundaries as observed in two-component system hydrogels, so that the gel does not cause absorption, irregular reflection or multiple reflection of light or sound.

The coupler for an ultrasonic diagnostic probe according to the present invention will be explained below.

Figure 1:
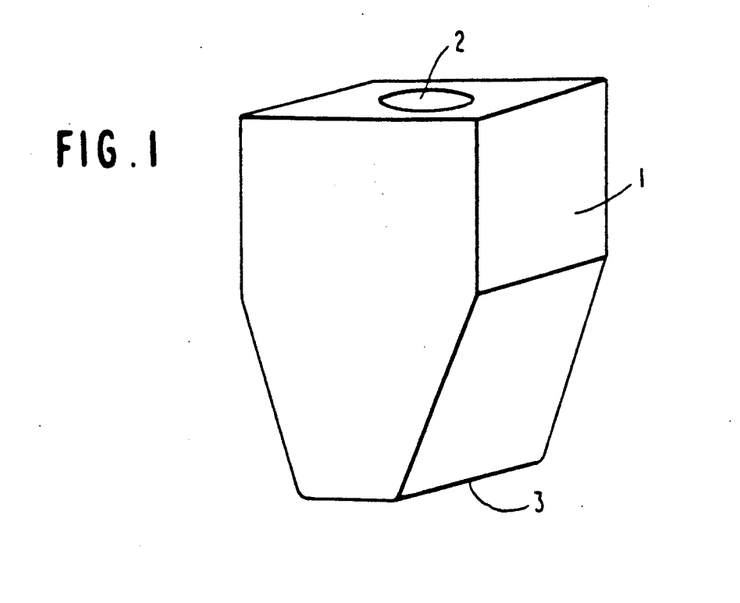
FIG. 1 is a perspective view of a coupler for an ultrasonic diagnostic probe according to the present invention.
Figure 2:
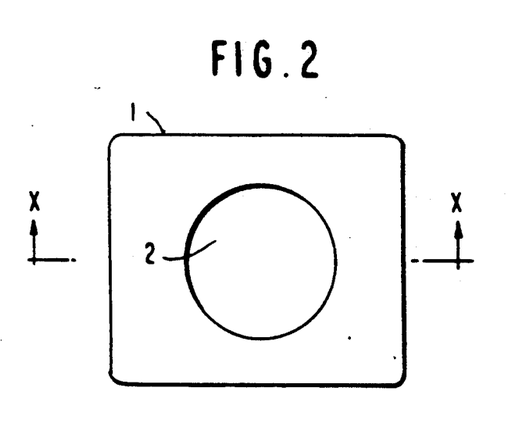
FIG. 2 is a plan view of the coupler of FIG. 1.
Figure 3:
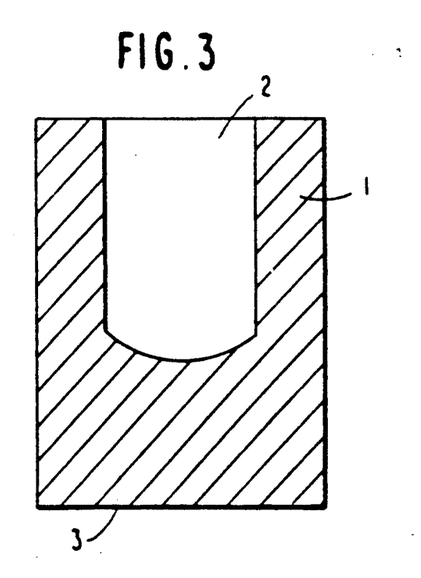
FIG. 3 is a cross section of FIG. 2 along the X—X line.

FIGS. 1 to 3 illustrate one embodiment of the coupler for ultrasonic diagnostic probes comprising a polyurethane gel of the present invention. The coupler is obtained by casting a mixture of the above-described room temperature liquid (AO) chain-containing polyol and/or room temperature liquid (AO) chain-containing polyurethane polyol prepolymer and the room temperature liquid (AO) chain-containing polyurethane polyisocyanate prepolymer in a mold of a prescribed shape to effect in-mold reaction. The size of coupler body 1 is, for example, 8 cm high, and 5 cm×6 cm at the upper part thereof. Socket 2 of 32 mm in diameter is formed on the top plane of coupler 1, into which a probe for ultrasonic diagnosis (not shown) is to be inserted. Socket 2 has the same shape as the probe to be inserted. The bottom of socket has such a shape for ensuring intimate contact with the probe. Numeral 3 indicates a smooth plane free from uneveness so as to ensure intimate contact with the site to be diagnosed without any gap therebetween. The coupler of this embodiment has a shape approximate to an inverted trapezoid, which is a design suited for inspection of the thyroid gland.

Figure 4:
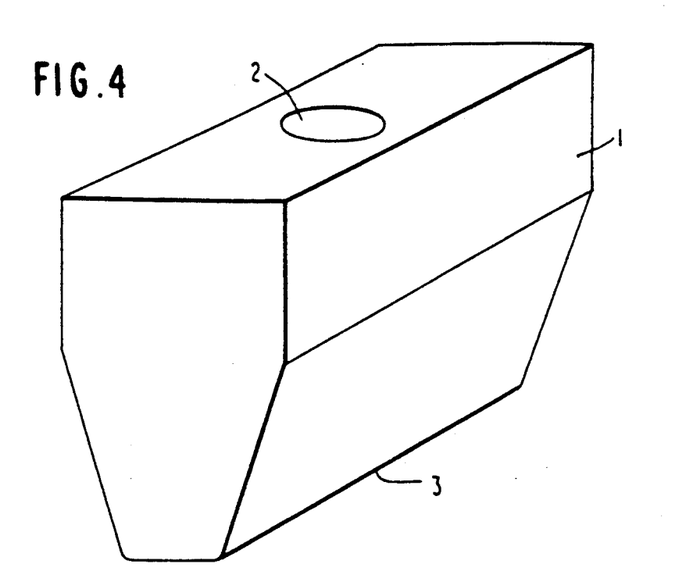
FIG. 4 is a perspective view of another coupler for an ultrasonic diagnostic probe according to the present invention.
Figure 5:
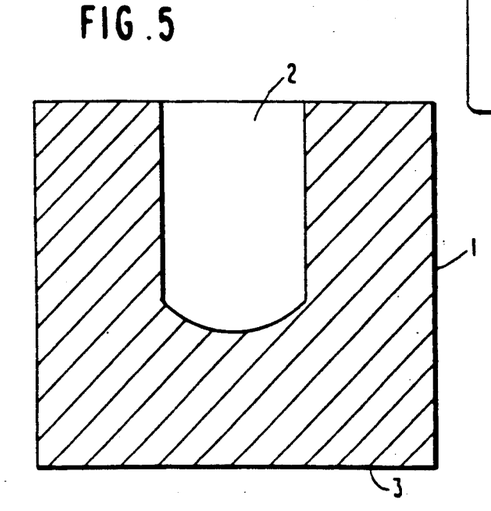
FIG. 5 is a cross section of FIG. 4 along the y—y line.
Figure 6:
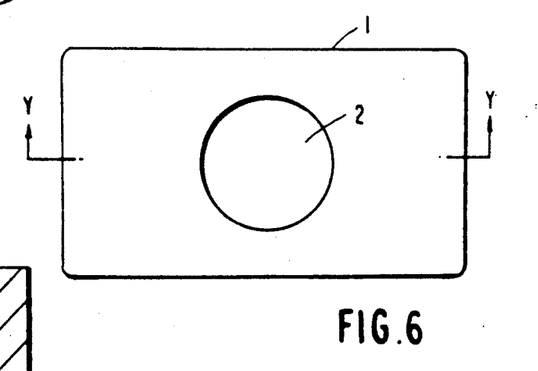
FIG. 6 is a plan view of the coupler of FIG. 4.

FIGS. 4 to 6 illustrate another embodiment of the coupler according to the present invention, which has the same construction as the one of FIGS. 1 to 3, except that the width is longer than the width of the coupler of FIGS. 1 to 3. This design is suited for inspection of the mammary gland.

Figure 7:
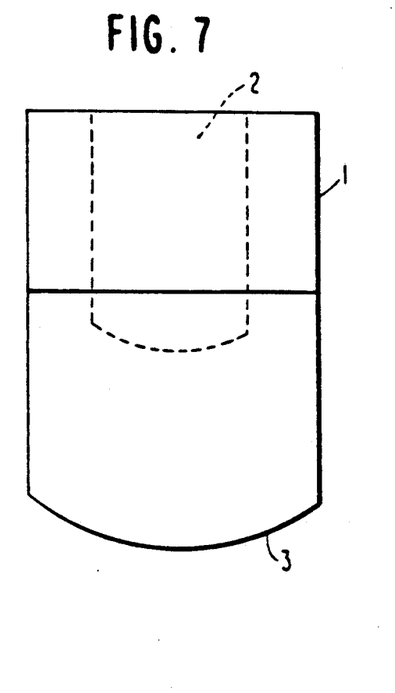
FIG. 7 is a perspective view of a still another coupler for an ultrasonic diagnostic probe according to the present invention.
Figure 8:
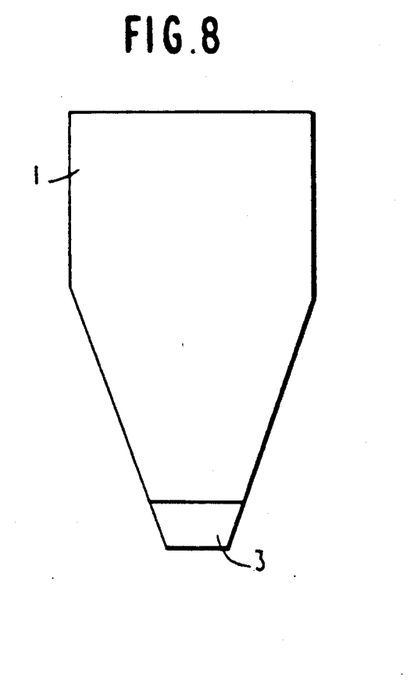
FIG. 8 is a side view of the coupler of FIG. 7.
Figure 9:
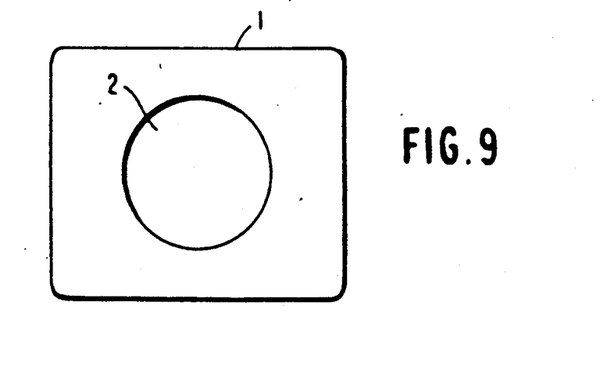
FIG. 9 is a plan view of the coupler of FIG. 7.
Figure 10A:
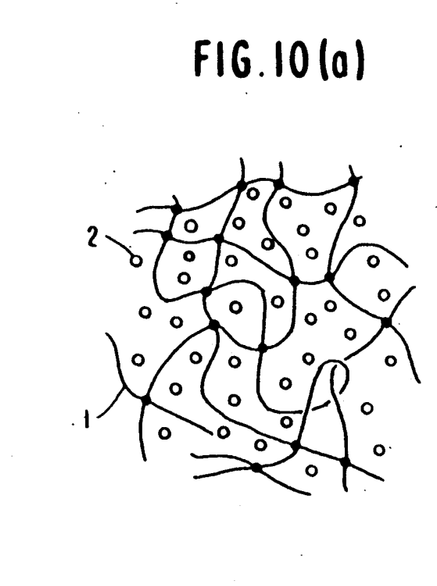
FIG. 10(a) is an illustrative structure of a conventional nonionic gel (organogel) wherein 1 represents a polymer chain and 2 represents water.
Figure 10B:
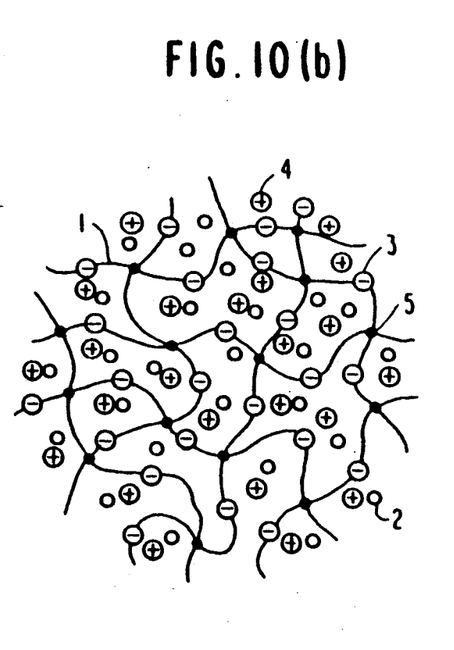
FIG. 10(b) is an illustrative structure of a conventional ionic gel wherein 1 represents a polymer chain, 2 represents water, 3 represents an ionic group, 4 represents a counter ion, and 5 represents a junction.
Figure 10C:
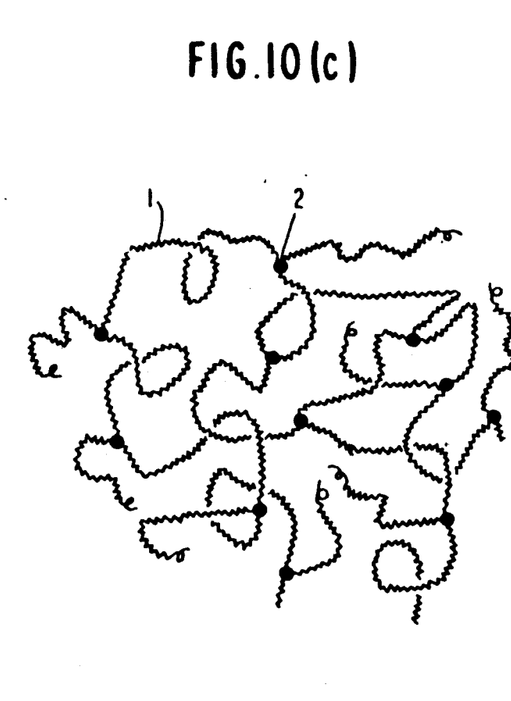
FIG. 10(c) is an illustrative structure of a liquid segment gel of the present invention wherein 1 represents a liquid segment and 2 represents a junction.

FIGS. 7 to 9 illustrate still another embodiment of the coupler according to the present invention, which has the same construction as the coupler of FIG. 1 to 3, except that smooth plane 3 is a curved surface so as to be fit for inspection of the carotid artery.

These couplers can easily be fixed to a probe for ultrasonic diagnosis simply by inserting the probe into socket 2. Since the coupler comprises the low-modulus polyurethane elastic gel, intimate contact between the probe and socket 2 or between smooth plane 3 and the site to be inspected can be assured. Ultrasonic diagnosis using the couplers of the present invention provides clear images free from noise and artifacts.

In the present invention, a stand off type in which a rectangular parallelpiped of the polyurethane gel according to the present invention is applied to the affected part of a body by using a probe can also be utilized.

Further, since the couplers made of the polyurethane gel of the invention do not cause bleeding of the dispersion medium as described above, they are of high safety, induce no allergic reaction of the skin even when kept in contact with the skin for an extended period of time, and give no irritation to the skin. Furthermore, these couplers show a rate of ultrasonic wave transmission which is very close to that of the human body tissues except bones and the lungs, are less dependent on frequency and cause relatively small attenuation of ultrasonic wave energy having a sonic impedance substantially equal to that of the human body tissues. That is, the couplers satisfy each of the main requirements needed for contact media for ultrasonic diagnosis on the practically acceptable level.

Furthermore, the couplers are excellent in preservation stability, being free from changes of physical properties, and satisfactory in shape retention, scratch resistance, stretch resistance, and abrasion resistance. They can thus withstand repeated use with economy.

Furthermore, the couplers can be produced in any desired shape with great ease simply by reacting a mixture of the polyol component and the polyisocyanate component in a prescribed casting mold.

The present invention is now illustrated in greater detail with reference to the following Examples, but it should be understood that the present invention is not deemed to be limited thereto. In these examples, all the parts are by weight unless otherwise indicated.

EXAMPLE 1

To a room temperature liquid polyether polyol component comprising 100 parts of a block copolymer comprising a polypropylene glycol (PPG) block (molecular weight (MW): 1000) and polyethylene glycol (PEG) blocks (MW: 335) at both ends of the PPG block and 33 parts of monomethoxypolyethylene glycol (MW: 400) were added 140 parts of a triisocyanate (MW: 3100) having room temperature liquid polyether polyol segments which was obtained by reacting an adduct of the PPG-PEG block copolymer and glycerin with hexamethylene diisocyanate (HMDI), 13 parts of a low-molecular weight diisocyanate, Duranate D201 (a trade name, produced by Asahi Chemical Industry Co., Ltd.), and 0.1 part of dibutyltin dilaurate as a catalyst, followed by stirring well. After thoroughly degassing the mixture under reduced pressure, the mixture was poured into a prescribed mold and allowed to stand at 60° C. for a whole day to obtain a coupler made of an elastic gel having the shape shown in FIG. 1.

The OH/NCO ratio of the elastic gel was 1.04. The sound velocity at 3.5 MHz and the damping factor in the elastic gel were 1474 m/sec and 0.73 dB/cm/MHz, respectively.

The elastic gel coupler exhibits adhesive properties on its surface and comes into intimate contact with the uneven surface of the skin. When the thyroid gland was inspected by ultrasonic waves of 7.5 MHz using a probe having fitted at the tip thereof the above obtained coupler, a clear image free from artifacts and noise was obtained. This is believed to be because the elastic gel was cast and cured with an extremely reduced strain. From the viewpoint of composition, the elastic gel is sanitary as it contains no low-molecular weight compound which may bleed out, i.e., no component which may stick to the skin, such as a plasticizer. It is not dried in air. It is extensible, soft, and very excellent in resistance to scratching and abrasion.

EXAMPLE 2

To a room temperature liquid polyether polyol component consisting of 36 parts of PEG (MW: 600) and 34 parts of monomethoxypolyethylene glycol (MW: 400) were added 76 parts of a triisocyanate (MW: 1606) obtained by addition reacting trimethylolpropane and polypropylene glycol and reacting the adduct with xylylene diisocyanate (XDI), and 0.3 part of dibutyltin dilaurate as a catalyst. The mixture was reacted in the same manner as in Example 1 to obtain an elastic gel coupler having the shape shown in FIG. 4. The OH/NCO ratio of the elastic gel was 1.44, and the weight ratio of (AO) to XDI was 3.6.

The resulting elastic gel shows a rate of ultrasonic wave transmission of 1459 m/sec at 3.5 MHz, that is very close to that of the human body, and the damping factor was 0.65 dB/cm/MHz.

When the above obtained elastic gel coupler was fitted at the tip of a mechanical sector probe, and the mammary-gland was inspected at 7.5 MHz, a diagnostic image of high quality free from artifacts or noise was obtained.

EXAMPLE 3

To a room temperature liquid polyether polyol component consisting of 110 parts of a PEG (MW: 100)/PPG (MW: 2000)/PEG (MW: 100) block copolymer (MW: 2200) and 80 parts of methoxypolyethylene glycol (MW: 400) were added 120 parts of a triisocyanate (MW: 1564) obtained by adding propylene glycol to glycerin and reacting the adduct with XDI and 0.2 part of dibutyltin dilaurate as a catalyst, and the mixture was reacted in the same manner as in Example 1 to obtain an elastic gel coupler having the shape shown in FIG. 7. The OH/NCO ratio was 1.30, and the (AO)/XDI weight ratio was 6.5.

The second velocity in the resulting elastic gel was 1454 m/sec with a damping factor being 0.67 dB/cm/MHz.

When the carotid artery was inspected at 7.5 MHz by using a probe having fitted at the tip thereof the above obtained elastic gel, the resulting image was of higher quality in freedom from artifacts and noise.

While the invention has been described in detail and with reference to specific embodiments thereof, it well be apparent to one skilled in the art that various changes and modifications can be made therein without departing from the spirit and scope thereof.

What is claimed is:

1. A coupler for a probe for ultrasonic diagnosis which comprises a liquid segment polyurethane gel obtained by reacting a polyol having an alkylene oxide chain which is liquid at room temperature and/or a polyurethane polyol prepolymer having an alkylene oxide chain which is liquid at room temperature with a polyurethane polyisocyanate prepolymer having an alkylene oxide chain which is liquid at room temperature, said gel having a socket into which the probe for ultrasonic diagnosis is to be inserted and a smooth part which is to be brought into planar contact with the skin.

2. A coupler as claimed in claim 1, wherein a ratio of terminal hydroxyl groups of said polyol and/or polyurethane polyol prepolymer to terminal isocyanato groups of said polyurethane polyisocyanate prepolymer, OH/NCO, is between 1 and 2.0.

3. A coupler as claimed in claim 1, wherein either one of said polyol and/or polyurethane polyol prepolymer and said polyurethane polyisocyanate prepolymer is at least bifunctional, with the other being at least trifunctional.

4. A coupler as claimed in claim 1, wherein said alkylene oxide chain in said polyol and/or polyurethane polyol prepolymer and said polurethane polyisocyanate prepolymer is selected from the group consisting of polymethylene glycol, polyethylene glycol, polypropylene glycol, polybutylene glycol, polytetramethylene glycol, polypentamethylene glycol, polyhexamethylene glycol, polyheptamethylene glycol, and a copolymer comprising two or more thereof.

5. A coupler as claimed in claim 1, wherein said polyol has a molecular weight of from about 150 to 6,000, said polyurethane polyol prepolymer has a molecular weight of from about 1,400 to 10,000, and said polyurethane polyisocyanate prepolymer has a molecular weight of from about 500 to 10,000.

6. A coupler as claimed in claim 1, wherein a proportion of the alkylene oxide chain in said gel is from about 75 to 90%.

* * * * *